(12) United States Patent
Favreau et al.

(10) Patent No.: US 12,127,742 B2
(45) Date of Patent: Oct. 29, 2024

(54) DEVICES, SYSTEMS, AND METHODS FOR CLOSING A WOUND

(71) Applicant: Boston Scientific Scimed, Inc., Maple Grove, MN (US)

(72) Inventors: John T. Favreau, Spencer, MA (US); Lauren S. Lydecker, Millbury, MA (US); Andrew Pic, Northboro, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 617 days.

(21) Appl. No.: 16/936,558

(22) Filed: Jul. 23, 2020

(65) Prior Publication Data

US 2021/0022740 A1 Jan. 28, 2021

Related U.S. Application Data

(60) Provisional application No. 62/879,218, filed on Jul. 26, 2019.

(51) Int. Cl.
*A61B 17/10* (2006.01)
*A61B 17/00* (2006.01)
(Continued)

(52) U.S. Cl.
CPC .......... *A61B 17/10* (2013.01); *A61B 17/0644* (2013.01); *A61B 2017/00296* (2013.01);
(Continued)

(58) Field of Classification Search
None
See application file for complete search history.

(56) References Cited

U.S. PATENT DOCUMENTS 5,478,353 A 12/1995 Yoon
5,624,453 A 4/1997 Ahmed
(Continued)

FOREIGN PATENT DOCUMENTS

CN 109833071 A 6/2019
EP 2073725 A2 7/2009
(Continued)

OTHER PUBLICATIONS

International Search Report and Written Opinion for the International Patent Application No. PCT/US2020/043171, mailed Dec. 21, 2020, 34 pages.

*Primary Examiner* — Shaun L David
(74) *Attorney, Agent, or Firm* — Seager, Tufte & Wickhem, LLP (57) ABSTRACT

The present disclosure pertains to medical devices. More particularly, the present disclosure pertains to devices, systems, and methods for closing a wound, such as a tissue defect resulting from an endoscopic mucosal resection or endoscopic submucosal dissection procedure. In one example, a device for closing a wound may include a closure element having a delivery configuration and a deployed configuration, the closure element configured to be disposed about an endcap of an endoscope in a delivery configuration. A release filament may have a distal end releasably coupled to the closure element and a proximal end extendable within the endcap. The closure element may be configured to substantially close about the wound in the deployed configuration.

9 Claims, 5 Drawing Sheets

(51) Int. Cl.
*A61B 17/04* (2006.01)
*A61B 17/064* (2006.01)
*A61B 17/08* (2006.01)
*A61B 17/30* (2006.01)

(52) U.S. Cl.
CPC .............. *A61B 2017/00867* (2013.01); *A61B 2017/0475* (2013.01); *A61B 2017/0649* (2013.01); *A61B 2017/081* (2013.01); *A61B 2017/306* (2013.01)

(56) References Cited

U.S. PATENT DOCUMENTS

| | | | | |
|---|---|---|---|---|
| 6,007,551 A | * | 12/1999 | Peifer | A61B 17/12013 606/139 |
| 6,042,591 A | * | 3/2000 | Mears | A61B 17/12013 606/140 |
| 6,059,797 A | * | 5/2000 | Mears | A61B 17/12009 606/139 |
| 8,021,362 B2 | | 9/2011 | Deem et al. | |
| 8,585,715 B2 | | 11/2013 | Hoffman et al. | |
| 9,072,517 B2 | | 7/2015 | Qadeer | |
| 9,295,463 B2 | | 3/2016 | Viola et al. | |
| 10,028,733 B2 | | 7/2018 | Bambury et al. | |
| 2002/0082641 A1 | | 6/2002 | Ginn et al. | |
| 2004/0006256 A1 | * | 1/2004 | Suzuki | A61B 1/00133 600/140 |
| 2005/0283188 A1 | | 12/2005 | Loshakove et al. | |
| 2006/0212071 A1 | | 9/2006 | Ginn et al. | |
| 2007/0093860 A1 | | 4/2007 | Rao et al. | |
| 2007/0225762 A1 | | 9/2007 | Labombard | |
| 2008/0287989 A1 | | 11/2008 | Weisel et al. | |
| 2010/0057101 A1 | * | 3/2010 | Karpiel | A61B 17/0643 606/140 |
| 2010/0057115 A1 | | 3/2010 | Rao et al. | |
| 2010/0114119 A1 | | 5/2010 | McLawhorn et al. | |
| 2012/0101521 A1 | | 4/2012 | Facchini De Souza et al. | |
| 2012/0150196 A1 | | 6/2012 | Hoffman et al. | |
| 2012/0239061 A1 | * | 9/2012 | Mathur | A61B 17/12013 606/140 |
| 2014/0039549 A1 | | 2/2014 | Belsky et al. | |
| 2015/0018848 A1 | | 1/2015 | Kappel et al. | |
| 2015/0366556 A1 | * | 12/2015 | Khairkhahan | A61B 17/0401 606/232 |
| 2016/0157858 A1 | | 6/2016 | Horton et al. | |
| 2016/0354192 A1 | | 12/2016 | Sniffin et al. | |
| 2016/0361066 A1 | * | 12/2016 | Wolfe | A61B 1/00133 |
| 2021/0128157 A1 | * | 5/2021 | Kikuchi | A61B 17/12013 |

FOREIGN PATENT DOCUMENTS

| | | |
|---|---|---|
| EP | 3019093 A1 | 5/2016 |
| JP | 2015524307 A | 8/2015 |
| JP | 2016526448 A | 9/2016 |
| WO | 2014018954 A1 | 1/2014 |

\* cited by examiner

DEVICES, SYSTEMS, AND METHODS FOR CLOSING A WOUND

PRIORITY

This application claims the benefit of priority under 35 U.S.C. § 119 to U.S. Provisional Patent Application Ser. No. 62/879,218, filed Jul. 26, 2019, which is incorporated by reference herein in its entirety and for all purposes.

FIELD

The present disclosure pertains to medical devices. More particularly, the present disclosure pertains to devices, systems, and methods for closing tissue, such as a tissue defect or wound resulting from an endoscopic procedure, e.g., a mucosal resection or endoscopic submucosal dissection procedure.

BACKGROUND

A tissue or opening or defect, for example a wound, such as a tissue defect within a body lumen resulting from endoscopic mucosal resection (EMR) or endoscopic submucosal dissection (ESD), may be large enough that it may be difficult to close on its own, or the time for it to close may be prolonged. A risk of infection may increase the longer the wound remains open. Wounds larger than an immediate working area of an endoscope may also be difficult to close using devices that are sized to extend through a working channel of an endoscope.

It is with the above considerations in mind that the improvements of the present disclosure may be useful.

SUMMARY

The present disclosure, in its various aspects, is directed generally to medical devices, and more specifically to devices, systems, and methods for closing a wound. In an aspect, a device for closing a wound may include a closure element that may have a delivery configuration and a deployed configuration. The closure element may be configured to be disposed about an endcap of an endoscope in the delivery configuration. A release filament having a distal end may be releasably coupled to the closure element and a proximal end that may be extendable within the endcap. The closure element may be configured to substantially close about the wound in the deployed configuration.

In various embodiments described here or otherwise, a plurality of the closure elements may each be separately and releasably coupled to the release filament in the delivery configuration about the end of the endoscope. The deployed configuration of the closure element may be a shape-memory configuration. The shape-memory configuration of the closure element may be a coil, a knot, or a torus, or a combination thereof. The closure element may extend along a length between terminal ends. The closure element may further include tissue-puncturing protrusions at each terminal end of the closure element. The tissue-puncturing protrusions may be hooks, tines, or barbs, or a combination thereof. The shape-memory configuration of the closure element may be activated by a stimulus. The stimulus may be light-activated, heat-activated, or electrically-activated, or a combination thereof. The distal end of the release filament may include a loop. The release filament may have a tensile strength that is greater than a tensile strength of the closure element. The loop may be disposed about a coil of the closure element. The loop may be disposed about a length of the closure element.

In an aspect, a device for closing a wound may include a closure element having an elongated un-activated configuration and an activated configuration. The closure element in the elongated un-activated configuration may be configured to be inserted into tissue edges opposing the wound. The closure element in the activated configuration may be configured to approximate the tissue edges to substantially close at least a portion of the wound.

In various embodiments described here or otherwise, the closure element may include a plurality of biodegradable portions interspersed between a plurality of adjacent light-activated shape-memory portions along a length of the closure element. The closure element may include first and second terminal ends configured to curl toward each other in the activated configuration. The activated configuration of the closure element may be a light-activated shape-memory configuration. The closure element may include a plurality of biodegradable portions interspersed between a plurality of adjacent light-activated shape-memory portions along a length of the closure element.

In an aspect, a method for closing a wound may include inserting a catheter into a patient. A distal end of the catheter may be oriented toward the wound. Suction may be applied to the wound such that the wound is at least partially displaced within the catheter. A self-contracting closure element may be deployed from about the catheter into the at least partially displaced wound within the catheter. Deploying the closure element may include actuating a release filament coupled to the closure element. Additional closure elements may be deployed from about the catheter that are each separately and releasably coupled to the release filament in a delivery configuration. Actuating the release filament may include proximally translating the release filament to deploy the closure element. The release filament may be proximally translated at least until the release filament decouples from the closure element. The catheter may be an endoscope. The closure element may be loaded about a cap attached to a distal end of the endoscope. A release filament may be backloaded through a working channel to a proximal end of the endoscope. The closure element may be removed from the patient after the wound has substantially healed. The self-contracting closure element may be activated with energy after the closure element has been deployed. A shape of the closure element may be a helix.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The detailed description should be read with reference to the drawings, which are not necessarily to scale, depict illustrative embodiments and are not intended to limit the scope of the invention.

A number of medical procedures, including intravascular procedures, procedures along the digestive, urinary, respiratory, reproductive and/or biliary tracts, thoracic procedures, etc., utilize medical devices to access tissue intended for removal (e.g., "target tissue") within the body. For example, in some current medical procedures (e.g., EMR and ESD), physicians may utilize an endoscope, colonoscope, duodenoscope, bronchoscope, gastroscope, or similar medical device to access and remove diseased lesions, creating a wound or defect in the tissue. A "wound" as used herein may include a defect, injury, bleed, ulcer, lumen opening, or like anatomy, which a medical professional would like to close for sealing, healing, hemostasis, ligation, or the like. In some instances, an endoscope may incorporate features which assist the physician in visualizing and performing the wound closing procedure. For example, some endoscopes may include a light and/or camera designed to illuminate and/or visualize the body lumen as the endoscope is navigated and positioned adjacent to a target tissue site. Additionally, some endoscopes may also include a lumen (e.g., a working channel) through which a resecting device, grasping member, or other accessory devices may be deployed and utilized. Additional visualization and/or external and/or internal imaging methods may be alternatively or additionally employed, e.g., fluoroscopy.

Medical procedures, e.g., EMR and ESD, may result in portions of tissue, e.g., body lumen or organ tissue, such as a mucosal layer, being resected and/or dissected, resulting in a wound or defect in the tissue. In this context, wound closure and healing may be aided by one or more devices substantially approximating wound tissue (e.g., wound edges) such that tissue layers are brought together or closer together across the wound for purposes, among others, of facilitating tissue adhesion and eventually healing of the wound, achieving hemostasis, or the like. Another consideration are wounds that are larger than an immediate working area of an endoscope, which may be difficult to close using devices that are sized to extend through a working channel of an endoscope, e.g., wounds larger than about 2 cm in diameter. These larger wounds may benefit from different configurations of closure devices and/or multiple closure devices as well.

The devices, systems, and methods of the present disclosure may be used alone or together with other devices, systems, and methods to treat wounds. Exemplary devices, systems, and methods with which embodiments of the present disclosure may be implemented include, but are not limited to, those described in U.S. patent application Ser. No. 13/325,638, titled "Endoscopic Apparatus with Integrated Variceal Ligation Device," filed Dec. 14, 2011, which is herein incorporated by reference in its entirety and for all purposes. Exemplary devices described therein may be modified to incorporate embodiments or one or more features of the present disclosure.

Figure 1A:
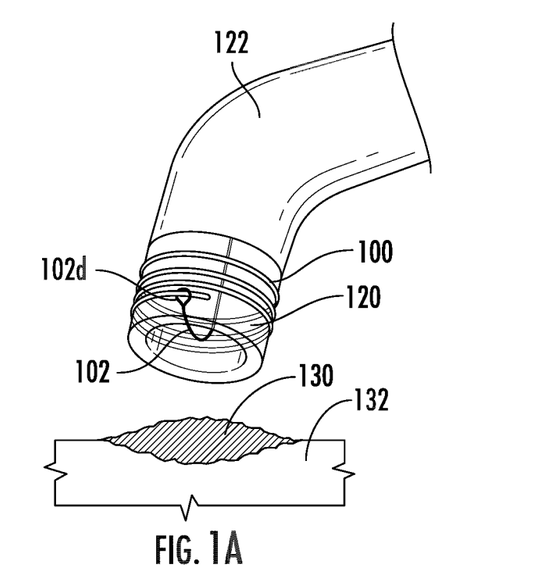
FIG. 1A illustrates an endoscope with a cap having a closure element oriented toward a wound, in accordance with an embodiment of the present disclosure.

Referring to FIG. 1A, a distal end of a device, e.g., an endoscope 122 for closing a wound 130 according to an embodiment of the present disclosure is illustrated, which includes a closure element 100 having a shape-memory configuration. The shape-memory configuration of the closure element 100 may be a helical coil when deployed, but other shapes are contemplated as described herein. The coils are wider in the delivery configuration than in the deployed configuration. The pitch of the coils is straight along a longitudinal axis of the closure element 100, but the coils may be pitched a number of degrees that may vary between the delivery configuration and the deployed configuration. For example, a pitch of the coils in the deployed configuration may be such that the helix is angled between about 0.01° and about 30°. The closure element 100 is delivered disposed about an endcap 120 of an endoscope 122. The endcap 120 may be an elongate hollow tube attachable to a distal end of the endoscope 122, such that any of a working channel, imaging device, and/or illumination device remain unobstructed when the endcap 120 is attached to the endoscope 122. A diameter of the coils in the relaxed, deployed configuration is less than a diameter of an outer surface of the endcap 120 such that the closure element 100 constricts around the endcap 120 in the delivery configuration. The endcap 120 positions the closure element 100 distal to and in view of an imaging device, e.g., a camera, of the endoscope 122 for a medical professional to visualize the closure element 100 and surrounding anatomy. The endcap 120 may be substantially translucent such that the medical professional may see through the endcap 120 to the closure element and surrounding anatomy. The closure element 100 is shown in a delivery configuration about the endcap 120 with a shape-memory spring force of the closure element 100 restrained by the diameter of the endoscope 122 shaft (or by the shaft of another delivery device, catheter, elongated member, or the like), such that the closure element 100 is extended to a diameter wide enough to fit about the endcap 120. The closure element 100 may be inserted into a body lumen of a patient in the delivery configuration about the endcap 120. A release filament 102 has a distal end 102*d* releasably coupled to the closure element 100 and a proximal end extending within the endcap 120. The proximal end of the release filament 102 may extend through the endoscope 122 and terminate outside of a proximal end of the endoscope 122. The proximal end of the release filament 102 may terminate at a handle or another device for actuation within or outside of the endoscope 122. The distal end 102*d* of the release filament 102 is a loop, but the distal end 102*d* may additionally or alternatively be other coupling mechanisms such as a weld, an adhesive, a hook, or like. The loop of the release filament may extend about more than one coil of the closure element 100 and may extend across the entire length of the closure element 100. The assembly of the closure element 100, release filament 102, and endcap 120 illustrated in FIG. 1A may be preloaded on the endoscope 122 prior to insertion into a patient. The endcap 120 may be oriented toward a wound 130 of a tissue 132 may a medical professional moving or translating the endoscope 122 within the patient.

Figure 1B:
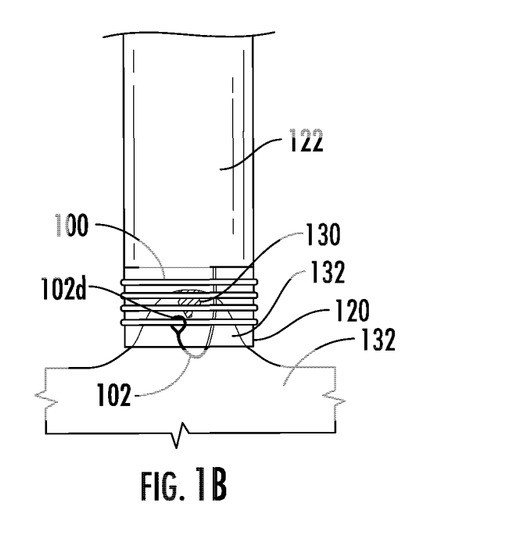
FIG. 1B illustrates the endoscope of FIG. 1A with the wound at least partially displaced within the cap of the endoscope.

Referring to FIG. 1B, the endcap 120 of the endoscope 122 may be placed about the wound 130, creating a substantial seal between the distal end of the endcap 120 and the tissue 132 surrounding the wound 130. The area within the endcap 120 may be suctioned via a suction and/or vacuum source that is in fluid communication with a suction channel of the endoscope 122. The suction force may create a negative pressure within the endcap 120 that displaces at least part of the wound 130 and surrounding tissue 132 proximally into the endcap 120. With the wound 130 at least partially displaced within the endcap 120, the distal end 102*d* of the release filament 102 remains extended out of the distal end of the endcap 120 and proximally along an outside of the endcap 120 to a point where the loop is coupled to the closure element 100 (disposed about the outside of the endcap 120 in the delivery configuration).

Figure 1C:
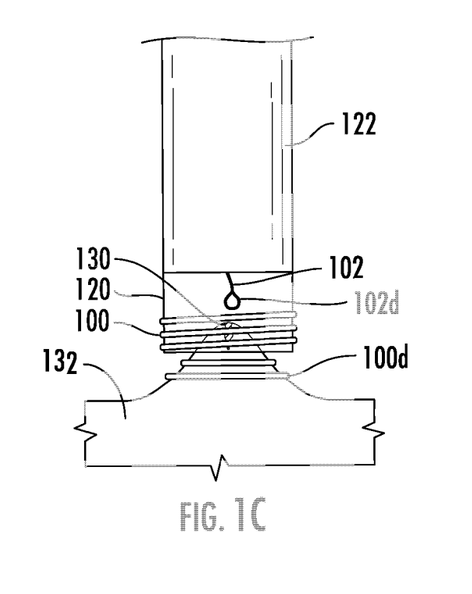
FIG. 1C illustrates the closure element of FIGS. 1A and 1B being deployed about the wound.

Referring to FIG. 1C, with the wound 130 and surrounding tissue 132 at least partially displaced proximally within the endcap 120, the release filament 102 may be translated (e.g., pulled) proximally to begin to transition the closure element 100 from the delivery configuration about the endcap 120, to a deployed configuration about the wound 130. In FIG. 1C, as the release filament 102 is translated proximally into the endcap 120, the distal end 102*d* of the release filament 102 displaces the distal end 100*d* of the closure element 100 off of the distal end of the endcap 120 and about the wound 130. The suctional force displacing the tissue 132 maintains the tissue 132 in tension allowing coils of the closure element 100 to constrict around margins of wound 130. A delivered closure element 100 has an inward closure force while the tissue 132 has a counter relaxing force against the closure element 100 resulting in a snug fit. The distal end 102*d* of the release filament 102 is decoupled (e.g., slid off of, broken away from, or the like) from the closure element 100 as the release filament 102 is translated proximally into the endcap 120. The distal end 102*d* of the release filament 102 may decouple from the end of the closure element 100 before the closure element 100 engages the tissue 132 or after the closure element 100 engages the tissue 132, e.g., the distal end 102*d* of the release filament 102 may slide off of the closure element 100 by temporarily disengaging a portion of the closure element 100 from the tissue 132 and thereafter the inward closure force of the closure element 100 reengages the tissue 132. As portions (e.g., windings of coils) of the closure element 100 (e.g., the distal end 100*d*) are released from the endcap 120 and about the wound 130, those portions of the closure element 100 transition from the stressed delivery configuration having a larger diameter to the un-stressed deployed configuration having a smaller diameter. The deployed configuration of the distal end 100*d* of the closure element 100 constricts about the wound 130 and surrounding tissue 132 due to the shape-memory configuration of the closure element 100. The deployed portion of the closure element constricting the tissue 132 anchors the distal end 100*d* of the closure element 100 such that the endoscope 122 may be translated proximally and the endcap 120 may be proximally pulled away from the distal end 100*d* as the remainder of the closure element 100 is released off of the endcap 120 and engaged about the wound 130.

Figure 1D:
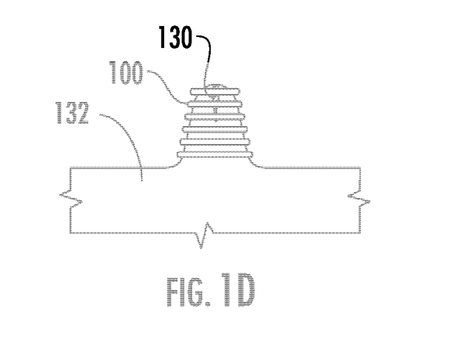
FIG. 1D illustrates the closure element of FIGS. 1A-1C deployed about the wound.

Referring to FIG. 1D, the closure element 100 is shown in the deployed configuration about the wound 130 and the surrounding tissue 132. The closure element 100 is not in a completely relaxed, unstressed state as the tissue 132 provides some resistance to the closure element 100 constricting the tissue 132. The closure element 100 in the deployed configuration may result in a substantially frustum shape having an apex over the wound 130 and away from the tissue 132. This shape is the result of a smaller volume of tissue 132 within the closure element 100 at the wound 130 site compared to the larger amount of tissue 132 within the closure element 100 away from the wound 130 site and/or the volume of tissue 132 displaced into the endcap 120. Alternatively, the closure element 100 may have a substantially cylindrical shape or inverted frustum shape (i.e., compared to the frustum shape of FIG. 1D) where a larger volume of tissue 132 is displaced such that there is more tissue displaced than illustrated in FIG. 1D. For example, a portion of the tissue 132 may extend proximally out of the closure device 100 that may form a bulbous or mushroom shape. The exposed area of the wound 130 is smaller and the edges of the wound 130 are closer together in FIG. 1C than the larger area and spread out edges of the wound 130 in FIG. 1A. As a diameter of the coils of the closure element 100 in the deployed configuration may decrease, a closure force in a radial direction toward the longitudinal axis of the closure element 100 may increase.

Figure 2A:
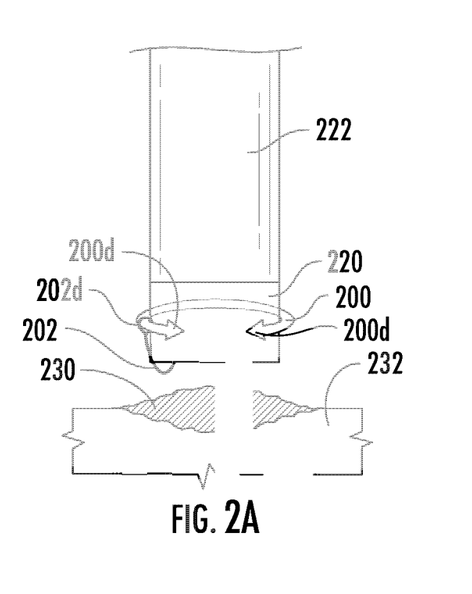
FIG. 2A illustrates an endoscope having a closure element oriented toward a wound, in accordance with an embodiment of the present disclosure.
Figure 2B:
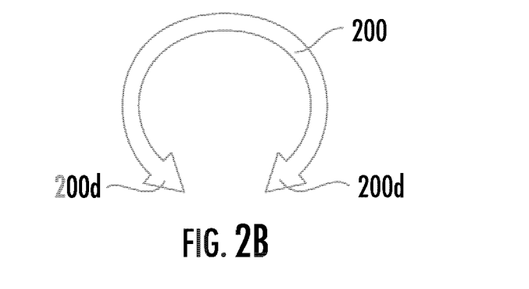
FIG. 2B illustrates the closure element of FIG. 2A in a deployed configuration.

Referring to FIGS. 2A and 2B, a device for closing a wound 230 is illustrated according to an embodiment of the present disclosure, which includes a closure element 200 having a shape-memory configuration. The shape-memory configuration of the closure element 200 is shown as a knot, but other shapes are contemplated as described herein. The closure element 200 includes a protrusion 200d at each end of the closure element 200 that is configured to penetrate or embed and engage into tissue. The illustrated protrusions 200d are barbs with arrowhead shape, but the protrusions 200d may be hooks, tines, or the like. The closure element 200 is disposed about an endcap 220 of an endoscope 222. The closure element 200 is shown in a delivery configuration about the endcap 220 with a shape-memory spring force of the closure element 200 expanding and stressing the closure element 200 to a diameter wide enough to fit about the endcap 220. The delivery configuration of the closure element 200 is illustrated in FIG. 2B. The closure element 200 may be inserted into a body lumen of a patient in the delivery configuration about the endcap 220. A release filament 202 has a distal end 202d releasably coupled to the closure element 200 and a proximal end extendable within the endcap 220. The distal end 202d of the release filament 202 is a loop, but the distal end 202d may additionally or alternatively be other releasable coupling mechanisms such as a spot weld, an adhesive, a hook, or like. The assembly of the closure element 200, release filament 202, and endcap 220 illustrated in FIG. 2A may be preloaded with the endoscope 222 prior to insertion into a patient. The endcap 220 may be oriented toward a wound 230 of a tissue 232.

Figure 2C:
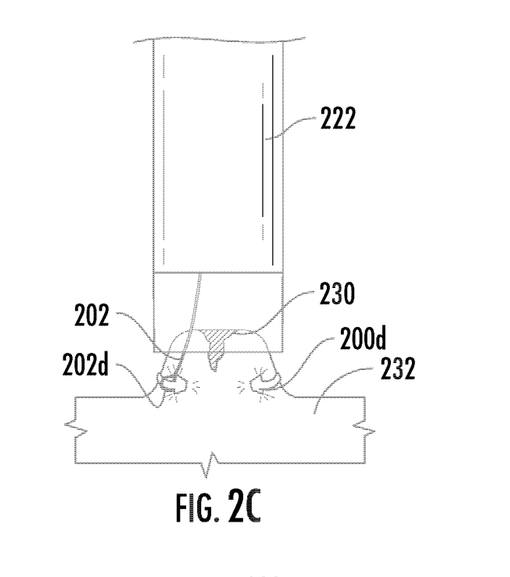
FIG. 2C illustrates the endoscope of FIG. 2A displacing the wound and the closure element of FIGS. 2A and 2B being deployed about the wound.

Referring to FIG. 2C, the endcap 220 of the endoscope 222 may be placed about the wound 230, creating a substantial seal between the distal end of the endcap 220 and the tissue 232 surrounding the wound 230. The area within the endcap 220 may be suctioned via a suction and/or vacuum source that is in fluid communication with a suction channel of the endoscope 222. The suction force may create a negative pressure within the endcap 220 that displaces at least part of the wound 230 and surrounding tissue 232 proximally into the endcap 220. With the wound 230 displaced into the endcap 220, the release filament 202 may be translated proximally to transition the closure element 200 from the delivery configuration about the endcap 220 to a deployed configuration about the wound 230. As illustrated in FIG. 2C, as the release filament 202 is translated proximally into the endcap 220, the distal end 202d of the release filament 202 displaces the closure element 200 off of the endcap 220 and about the wound 230. The distal end 202d of the release filament 202 is decoupled (e.g., slid off of, broken or cut away from, or the like) from the closure element 200 as the release filament 202 is translated proximally into the endcap 220. The distal end 202d of the release filament 202 may decouple from the end of the closure element 200 before the closure element 200 engages the tissue 232 or after the closure element 200 engages the tissue 232, e.g., the distal end 202d of the release filament 202 may slide off of the closure element 200 by temporarily disengaging a portion of the closure element 200 from the tissue 232 and thereafter the inward closure force of the closure element 200 reengages the tissue 232. The release filament may decouple from the closure element 200 by breaking from engaging with the protrusion 200d. As the closure element 200 is displaced off of the endcap 220 and about the wound 230, the closure element 200 transitions from the extended delivery configuration having a greater diameter to the un-extended deployed configuration having a lesser diameter.

Figure 2D:
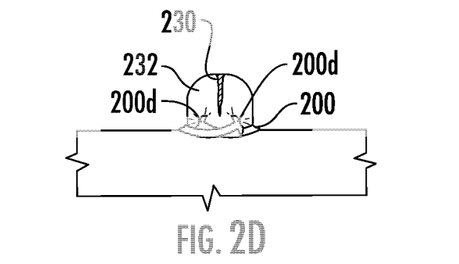
FIG. 2D illustrates the closure element of FIGS. 2A-2C deployed about the wound.
Figure 2E:
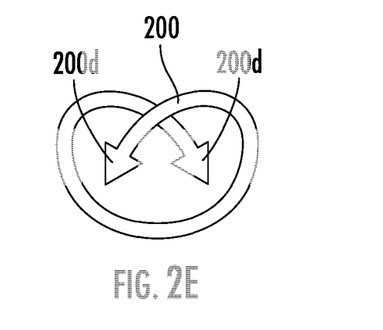
FIG. 2E illustrates the closure element of FIGS. 2A-2D in a delivery configuration.

Referring to FIGS. 2D and 2E, the deployed configuration of the closure element 200 constricts about the wound 230 and surrounding tissue 232 due to the shape-memory of the closure element 200. The deployed configuration of the closure element 200 is illustrated in FIG. 2E. In the deployed configuration, the closure element transitions to the unstressed, knotted shape-memory orientation (e.g., knotted, pretzel-like, etc.) with the protrusions 200d oriented internally to the closure element 200d such that a portion of the length of the closure element 200 overlaps with itself. The protrusions 200d may fully embed, partially embed, or not embed into the tissue 232.

Figure 3A:
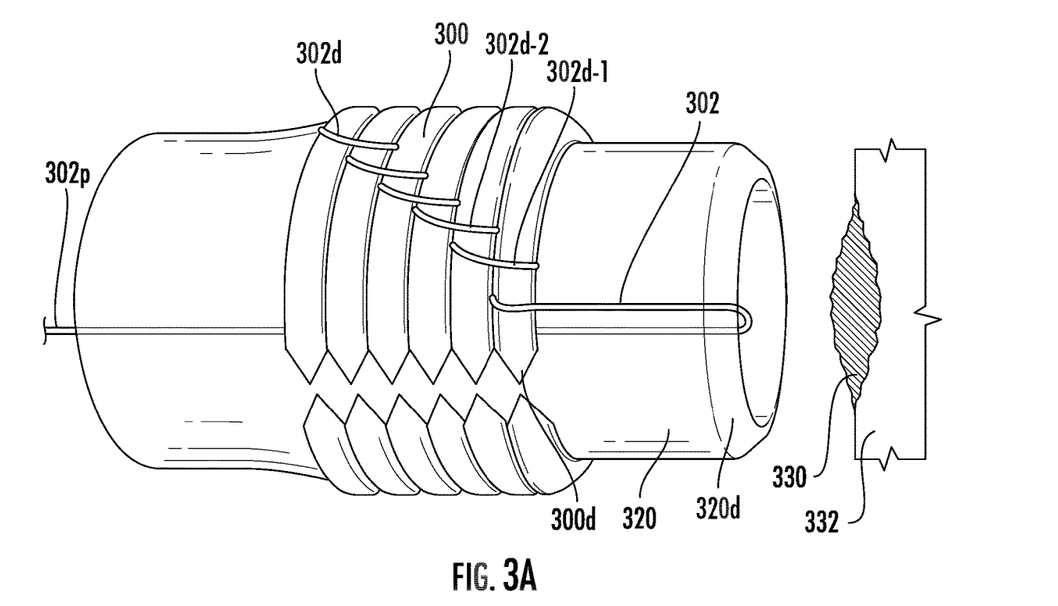
FIG. 3A illustrates an endcap having a plurality of closure elements, in accordance with an embodiment of the present disclosure.
Figure 3B:
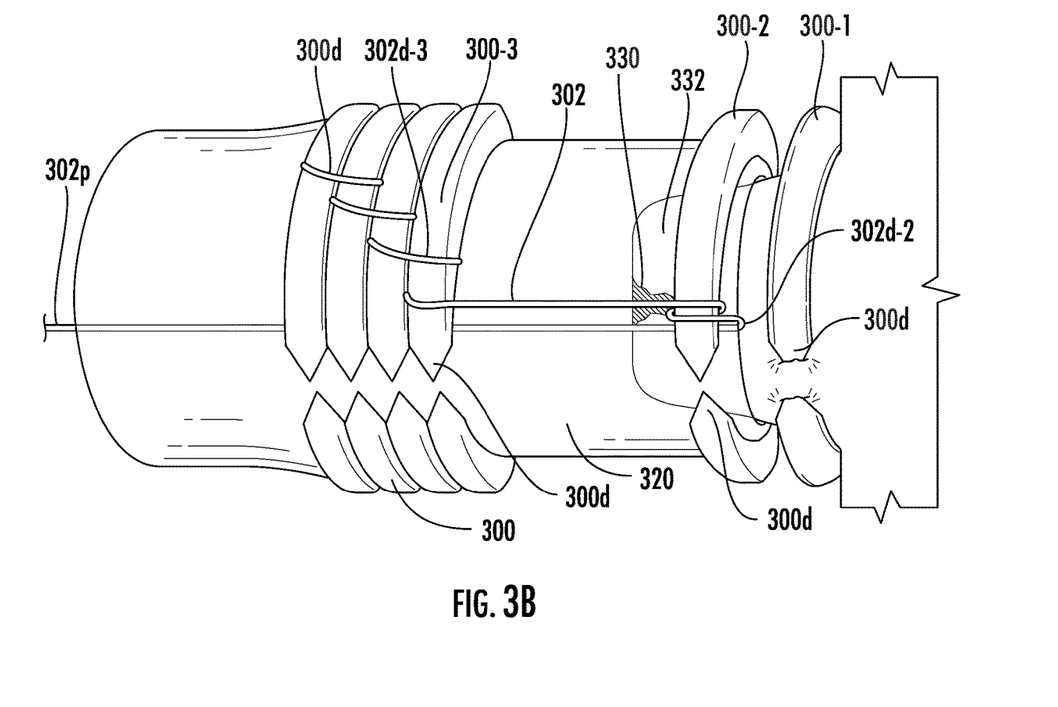
FIG. 3B illustrates the endcap of FIG. 3A deploying a closure element.

Referring to FIGS. 3A and 3B, a device for closing a wound 330 according to an embodiment of the present disclosure is illustrated, which includes multiple closure elements 300 disposed about an endcap 320 in a delivery configuration. The closure elements 300 each include a protrusion 300d at each end of the closure element 300 that are configured to penetrate or embed and engage tissue. The protrusions 300d are barbs, but the protrusions 300d may be hooks, tines, or the like. The device includes a release filament 302 that has a distal portion that is coupled to each of the closure elements 300 by a series of loops 302d. A release filament as described elsewhere in this disclosure may be used in a substantially similar manner as the release filament 302 illustrated in FIGS. 3A and 3B (e.g., the release filament 102 with loops about each winding of the release filament 102 or one or more release filament 202). Each loop 302d of the release filament 302 extends independently around each closure element 300 while the closure elements 300 are in the delivery configuration. The release filament 302 has a proximal portion 302p that extends within the endcap 320. A proximal translation of the proximal portion 302p of the release filament 302 translates a pulling force to the distal-most loop 302d-1 because the release filament 302 extends from within the endcap 320 to outside of the endcap by extending over a distal end 320d of the endcap 320. The distal end 320d of the endcap 320 may be oriented toward, about, and/or in contact with a wound 330 and/or the surrounding tissue 332. A suction force may be introduced in fluid communication with the endcap 320 to displace the wound 330 into the endcap 320, as illustrated in FIG. 3B. The release filament 302 may be translated proximally such that a distal-most loop 300d pulls a respective closure element 300 distally along the outside of the endcap 320. The release filament 302 may be continually translated proximally such that the distal-most closure element 300 is displaced off of the endcap 320 and transitions from the delivery configuration to the deployed configuration. As illustrated in FIG. 3B, the closure element 300-1 is deployed into the tissue 332. A proximal translation of the proximal portion 302p of the release filament 302 displaces the distal-most loop 302d-2 along with the closure element 300-2 distally along the endcap 320. As the closure element 300-2 is displaced off of the distal end 320d of the endcap 320, the closure element 300-2 begins to transition from the delivery configuration to the deployed configuration and the loop 302d-2 begins to de-couple from the closure element 300-2. After deployment of the closure element 300-2, the distal-most closure element 300-3 may be deployed at the same tissue 332 location or to another tissue location by proximally translating the proximal portion 302p such that the distal-most loop 302d-3 may be displaced.

Figures 4A, 4B:
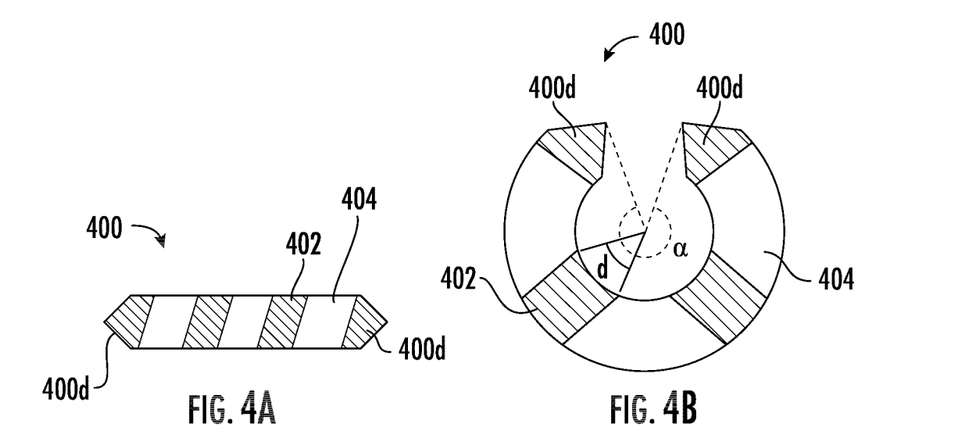
FIG. 4A illustrates a closure element in an un-activated, delivery configuration, in accordance with an embodiment of the present disclosure.
FIG. 4B illustrates the closure element of FIG. 4A in an activated configuration.

With reference to FIGS. 4A and 4B, a device according to an embodiment of the present disclosure is illustrated including a closure element 400. The closure element 400 has an elongated, un-activated configuration illustrated in FIG. 4A and a curved, activated configuration illustrated in FIG. 4B. In the un-activated configuration, the closure element 400 extends substantially linearly from one end 400d of the closure element 400 to the other end 400d. In the activated configuration, the ends 400d of the closure element 400 curl toward each other. The activated configuration of the closure element 400 is shown as substantially "C-shaped", but the activated configuration could be a variety of shapes, e.g., "U-shaped", "S-shaped", "Z-shaped", or combinations thereof, etc. The closure element 400 includes a plurality of activatable portions 402 along a length of the closure element 400. Although four activatable portions 402 are depicted, any number of activatable portions 402 may be utilized, e.g., 1, 2, 3, 5, 8, 10, 20, 100, 1000, etc. Additionally, or in the alternative, the activatable portions 402 may blend into other portions of the closure element 400 such that they mix. A blend of portions may comprise a substantially uniform mixture throughout the blend or the blend may have a varying percentage of each of the portions that increases or decreases along a length of the closure element 400. The activatable portions 402 may be sensitive to activation from an external stimulus source such as heat, light, infrared light, electricity, energy, pH, or the like that may cause the activatable portions 402 to alter the geometric shape of the closure element 400. Activatable portions 402 may be patterned along the closure element 400 at specific locations to act as actuating hinges or fold points at or along which the shape of the closure element 400 can deform into the activated (e.g., curved) configuration. Each activatable portion 402 may contract a number of degrees d (e.g., about 0° to about 360°) such that the closure element 400 in the activated configuration has an overall curvature a equal to the number of degrees d multiplied by the number of activatable portions 402. The activatclosure element 400 (or other closure elements described herein) may also include biodegradable portions 404 along the length of the closure element 400. A closure element 400 may comprise of only activatable portions, only biodegradable portions, or neither. The portions may be located at different places along the length of a closure element 400 and may have arrangements other than those depicted in the figures. For example, one or more protrusions of a closure element may be non-biodegradable with the remainder of the closure element being biodegradable such that the one or more protrusions remain in tissue while the remainder of the closure element is passed. The biodegradable portions 404 may degrade over time after deployment into a patient such that as a wound associated with the closure element 400 heals and the closure element 400 is no longer needed (e.g., within about seven days, within about fourteen days, within about a month, within about a plurality of months, within about a year, etc., depending on the materials used and depending on characteristics of the wounds), the biodegradable portions 404 may degrade sufficiently such that the closure element 400 falls away from the tissue. Although three biodegradable portions 404 are depicted, any number of biodegradable portions 404 may be utilized, e.g., 1, 2, 4, 5, 8, 10, 20, 100, 1000, etc. Additionally, or in the alternative, the biodegradable portions 404 may blend into other portions of the closure filament 400 such that they mix. The biodegradable portions 404 or other portions may include drugs that may assist a wound or may be otherwise released into the body of a patient (e.g., analgesic, healing, antibacterial, etc.) The ends 400d each include a protrusion that are configured to penetrate, or embed and engage, tissue. The protrusions are shown as sharpened points, but may also be barbs, but may be hooks, tines, or the like.

Figure 4C:
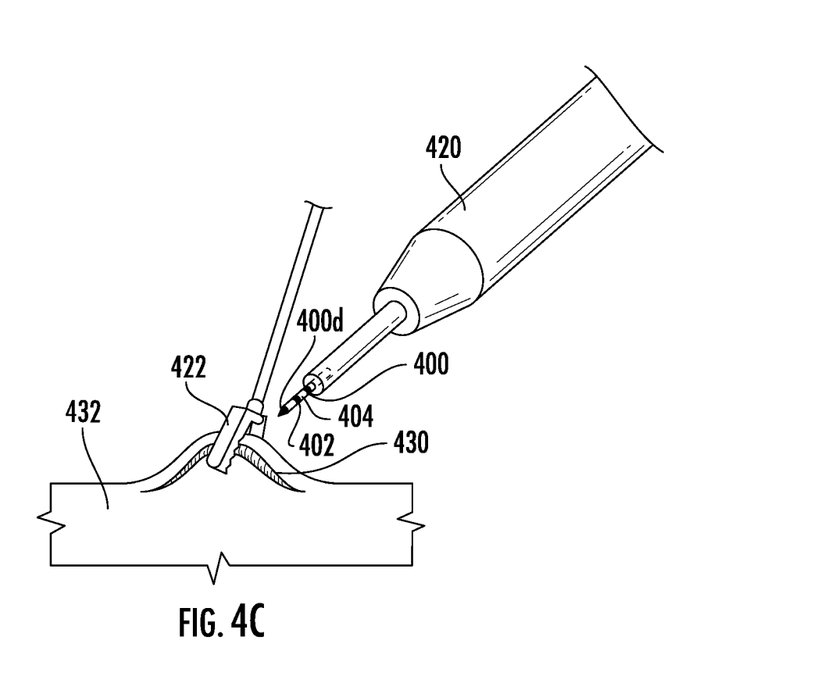
FIG. 4C illustrates the closure element of FIGS. 4A and 4B oriented toward a wound.
Figure 4D:
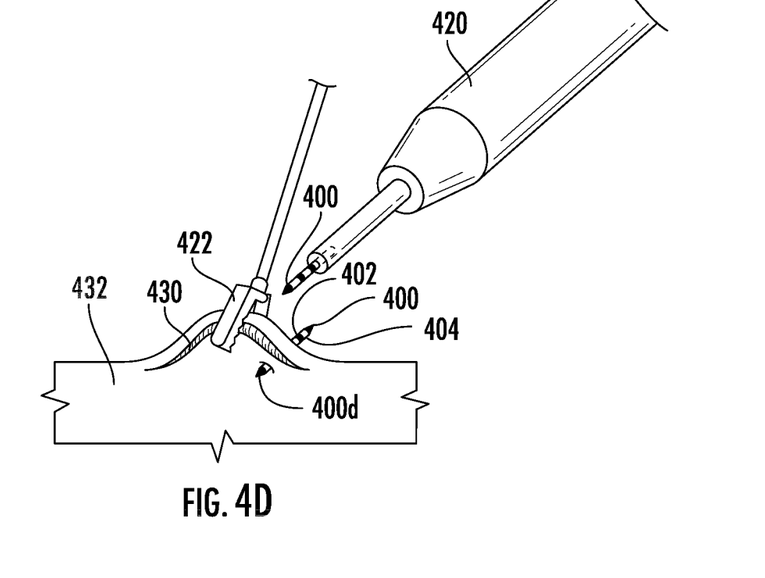
FIG. 4D illustrates the closure element of FIGS. 4A-4C delivered about the wound.
Figure 4E:
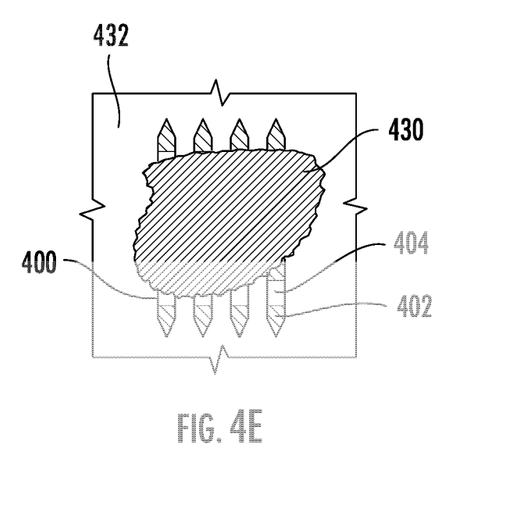
FIG. 4E illustrates multiple closure elements of FIGS. 4A-4D delivered about the wound.
Figure 4F:
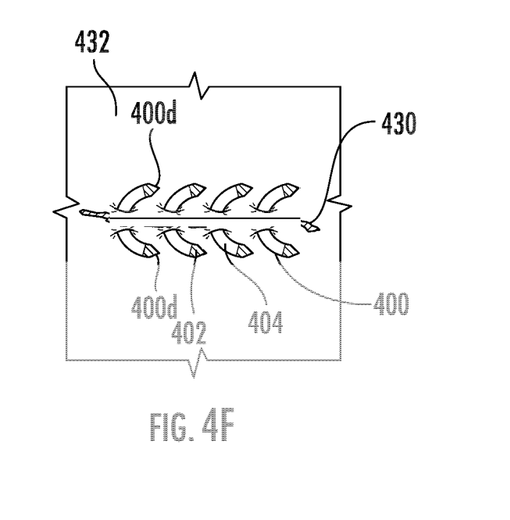
FIG. 4F illustrates the closure elements of FIGS. 4A-4E in an activated configuration.

With reference to FIGS. 4C-4F, the closure element 400 of FIGS. 4A and 4B may be used to close a wound 430. As illustrated in FIG. 4C, the wound 430 and a surrounding tissue 432 may be displaced via a medical instrument 422 (e.g., a grasper, a working channel with a suctioning force, a clip, or the like). A delivery device 420 (e.g., a needle, a catheter, or the like) having a closure element 400 in the elongated un-activated configuration is configured for tissue insertion and may be oriented toward the wound 430 and tissue 432. As illustrated in FIG. 4D, a closure element 400 may be delivered into the tissue 432 across the wound 430 by leading with a protrusion on an end 400d of the closure element 400. The tissue 432 may be displaced (e.g., tissue edges approximated) by the medical instrument 422 (e.g., forceps or grasper) to allows the end 400d of the closure element 400 to puncture through two sides of the tissue 432 about the wound 430 in one insertion motion along a longitudinal axis of the closure element 400. An additional closure element 400 may be delivered from the delivery device 420 such that multiple closure elements 400 are delivered into the tissue 432 across the wound 430, as illustrated in FIG. 4E (with the tissue 432 released from the medical instrument 422). Although four closure elements 400 are illustrated in FIG. 4E, any number of closure elements 400 may be used, e.g., 1, 2, 3, 5, 8, 10, 20, 100, a number such the closure elements 400 extend across a substantial area of the wound 430, etc. The closure elements 400 after being delivered are illustrated in the un-activated configuration in FIG. 4E. An activator external to the closure element 400 may activate the activatable portions 402 of each closure element 400 such that they transition from the un-activated configuration to the activated configuration. The activated configuration of the closure elements 400 across the wound 430 is illustrated in FIG. 4F. The activatable portions 402 are contracted such that the ends 400d are curled toward each other and the wound 430 is substantially closed or closed such that edges of the wound 430 are closer together than in FIG. 4E. Over time, the biodegradable portions 404 may degrade such that the closure members 400 fall away from the tissue 432. Alternatively, no portion of the closure members 400 may degrade, and as the wound 430 heals, scabs, scars, and/or sloughs off, the closure members 400 may fall away from the tissue 432.

In various embodiments, a medical professional may attach an endcap to an endoscope, a catheter, or the like. The medical professional may load one or more closure elements onto the endcap. The one or more closure elements may be releasably coupled to a release filament extending within the endcap and may be attached to a handle. The endoscope and assembly may be inserted into a patient. A target wound may be located. The endcap may be oriented toward the wound. The wound or surrounding tissue may be displaced into the endcap. The one or more closure elements may be released about the wound by the medical professional manipulating the release filament.

In various embodiments, a medical professional may insert one or more un-activated closure elements within a delivery device, such as a needle. The delivery device may be inserted into a patient. A target wound may be located. The delivery device may be oriented toward the wound. The one or more closure elements may be deployed into a tissue about the wound. The one or more closure elements may be activated such that the one or more closure elements transition from the un-activated configuration to an activated configuration.

In various embodiments, a closure element may comprise a shape-memory material such as nitinol, stainless steel, nickel titanium, an alloy, a polymer, a rubber, nylon, combinations thereof, or the like. Closure elements may have a shape and/or shape-memory set by a mandrel. Shapes of a closure element may include a coil, a helix, a knot, a pretzel, a straight line, "C-shaped", "V-shaped", "U-shaped", "S-shaped", "Z-shaped", a combination thereof, or the like. A closure element may be heat set at a diameter (e.g., a diameter of about 1 mm to about 5 mm, or the like) that may be selectable based on wound geometry and size.

In various embodiments, an endcap as described and illustrated herein may be coupled to an endoscope, catheter, and/or working channel (e.g., insertable, adhered, manufactured as a unibody, etc.). An endcap may additionally or in the alternative be an extension of an endoscope, catheter, and/or working channel.

Devices according to the embodiments described, and in accordance with other embodiments of the present disclosure, alone or in a system or kit or as part of a method or procedure, including with other accessories, may be used in cavities, lumens, tracts, vessels and organs of the body, such as to access, treat or diagnose conditions in the peritoneal, abdominal, bronchial or thoracic cavities, vascular vessels, gastrointestinal or urinary tract, uterus, bladder, lung and liver organs, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A device for closing a wound, comprising:
    a closure element having a delivery configuration and a deployed configuration, the closure element configured to extend circumferentially over and around the exterior of an endcap of an endoscope in the delivery configuration and having a first terminal end and a second terminal end spaced apart from each other and positioned over the exterior of the end cap, the first terminal end having a first protrusion configured to engage tissue and the second terminal end having a second protrusion configured to engage tissue; and
    a release filament having a distal end releasably coupled to the closure element and a proximal end extendable within the endcap;
    wherein the deployed configuration of the closure element is a shape-memory configuration configured to substantially close about the wound in the deployed configuration.

2. The device of claim 1, further comprising a plurality of the closure elements that are each separately and releasably coupled to the release filament in the delivery configuration about the end of the endoscope.

3. The device of claim 1, wherein the shape-memory configuration of the closure element is a coil, a knot, or a torus, or a combination thereof.

4. The device of claim 1, wherein at least one of the first or second protrusion is configured to puncture tissue.

5. The device of claim 4, wherein the tissue-puncturing protrusions are hooks, tines, or barbs, or a combination thereof.

6. The device of claim 1, wherein the shape-memory configuration of the closure element is activated by a stimulus, the stimulus comprising light-activated, heat-activated, or electrically-activated, or a combination thereof.

7. The device of claim 1, wherein the distal end of the release filament comprises a loop.

8. The device of claim 1, wherein the release filament has a tensile strength that is greater than a tensile strength of the closure element.

9. The device of claim 1, wherein, when in the shape memory configuration, the closure element is configured to encircle the wound.

* * * * *